United States Patent
DeTroy (10) Patent No.: US 9,913,972 B2
(45) Date of Patent: Mar. 13, 2018

(54) CANNULA SEAL

(71) Applicant: INTUITIVE SURGICAL OPERATIONS, INC., Sunnyvale, CA (US)

(72) Inventor: David DeTroy, Norwalk, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 245 days.

(21) Appl. No.: 14/020,561

(22) Filed: Sep. 6, 2013

(65) Prior Publication Data
US 2014/0074035 A1    Mar. 13, 2014

Related U.S. Application Data

(60) Provisional application No. 61/698,448, filed on Sep. 7, 2012.

(51) Int. Cl.
*A61M 39/26* (2006.01)
*A61M 39/20* (2006.01)
(Continued)

(52) U.S. Cl.
CPC .......... *A61M 39/26* (2013.01); *A61M 39/20* (2013.01); *A61M 2039/064* (2013.01);
(Continued)

(58) Field of Classification Search
CPC .......... A61B 17/3462; A61B 17/3498; A61B 17/3421; A61B 17/3415; A61B 2017/3419; A61M 39/06; A61M 39/0613; A61M 39/0606; A61M 2039/0646; A61M 2039/0633; A61M 2039/0626; A61M 2039/0686; A61M 2039/064;
(Continued)

(56) References Cited

U.S. PATENT DOCUMENTS 4,960,412 A    10/1990  Fink
5,092,857 A *  3/1992  Fleischhacker ... A61M 39/0606
                                                      137/846
(Continued)

FOREIGN PATENT DOCUMENTS

EP    2143393 A1    1/2010
EP    2143393 A1    1/2010
(Continued)

OTHER PUBLICATIONS

International Search Report and Written Opinion for Application No. PCT/US13/58617, dated Dec. 11, 2013, 12 pages.
(Continued)

*Primary Examiner* — Lauren P Farrar
(74) *Attorney, Agent, or Firm* — Schwegman Lundberg & Woessner, P.A.

(57) ABSTRACT

A cannula seal is presented. The cannula seal includes a cap portion that fits over a cannula and a valve portion. The valve portion includes an hourglass seal and a cross slit seal. In some embodiments, the cap portion includes a tab. In some embodiments, the cap portion and the valve portion are integrally formed. In some embodiments, the cap portion and the valve portion are joined at a bonding region, which may include overflow traps. In some embodiments, ribs are included.

11 Claims, 5 Drawing Sheets

(51) Int. Cl.
*A61M 39/06* (2006.01)
*A61M 39/24* (2006.01)

(52) U.S. Cl.
CPC .............. *A61M 2039/0646* (2013.01); *A61M 2039/0686* (2013.01); *A61M 2039/2433* (2013.01)

(58) Field of Classification Search
CPC .......... A61M 2039/0673; A61M 39/02; A61M 39/26; A61M 39/20; A61M 2039/2433
USPC ........................ 604/167.01, 167.04, 167.03
See application file for complete search history.

(56) References Cited

U.S. PATENT DOCUMENTS

| | | | | |
|---|---|---|---|---|
| 5,141,498 | A * | 8/1992 | Christian | A61M 39/06 251/149.1 |
| 5,197,955 | A * | 3/1993 | Stephens | A61B 17/3462 604/167.01 |
| 5,269,763 | A | 12/1993 | Boehmer et al. | |
| 5,330,437 | A * | 7/1994 | Durman | A61M 39/06 137/846 |
| 5,814,026 | A | 9/1998 | Yoon | |
| 7,112,185 | B2 | 9/2006 | Hart et al. | |
| 8,109,910 | B2 | 2/2012 | Zastawny et al. | |
| 8,109,911 | B2 * | 2/2012 | Taylor | A61B 17/3462 604/167.06 |
| 2004/0111060 | A1 * | 6/2004 | Racenet | A61B 17/34 604/167.01 |
| 2004/0254534 | A1 * | 12/2004 | Bjorkman | A61M 39/0606 604/160 |
| 2004/0260243 | A1 * | 12/2004 | Rickerd | A61M 39/0606 604/161 |
| 2005/0065475 | A1 * | 3/2005 | Hart | A61B 17/3462 604/167.06 |
| 2006/0149294 | A1 | 7/2006 | Argentine et al. | |
| 2006/0211992 | A1 * | 9/2006 | Prosek | A61B 17/3498 604/167.06 |
| 2008/0051739 | A1 | 2/2008 | McFarlane | |
| 2008/0077169 | A1 * | 3/2008 | Taylor | A61B 17/3462 606/185 |
| 2008/0157017 | A1 * | 7/2008 | Macatangay et al. | 251/314 |
| 2009/0234291 | A1 * | 9/2009 | Saunders | A61M 25/0693 604/167.01 |
| 2010/0004599 | A1 * | 1/2010 | Zhou et al. | 604/167.04 |
| 2010/0016799 | A1 * | 1/2010 | Schweitzer | A61B 17/3462 604/167.01 |
| 2010/0274193 | A1 | 10/2010 | Patton et al. | |
| 2011/0009703 | A1 | 1/2011 | Smith | |

FOREIGN PATENT DOCUMENTS

| | | |
|---|---|---|
| EP | 2305148 A1 | 4/2011 |
| EP | 2305148 A1 | 4/2011 |
| WO | WO-9532019 A1 | 11/1995 |
| WO | WO-9532019 A1 | 11/1995 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP13835879, dated Feb. 3, 2016, 8 pages.

"European Application Serial No. 13835879.1, Extended European Search Report dated Feb. 3, 2016", 7 pgs.

* cited by examiner

CANNULA SEAL

RELATED APPLICATIONS

This application claims priority to U.S. Provisional Application Ser. No. 61/698,448, filed on Sep. 7, 2012, which is herein incorporated by reference in its entirety.

TECHNICAL FIELD

Embodiments of the present invention are related to surgery and, in particular, to a cannula seal.

DISCUSSION OF RELATED ART

Minimally invasive surgery (e.g., endoscopy, laparoscopy, thoracoscopy, cystoscopy, and the like) allows a patient to be operated upon through one or more small incisions or a natural body orifice by using elongated surgical instruments introduced to an internal surgical site. In many instances, an imaging device is also introduced to the surgical site in the same way so that a surgeon may see the instruments while working at the surgical site. The surgical site is often located inside a body cavity, such as the patient's abdomen. The body cavity may optionally be distended using a clear fluid such as an insufflation gas, typically $CO_2$. In traditional minimally invasive surgery, the one or more surgical instruments are inserted through a cannula in order to reach the surgical site. Each cannula is inserted into an incision made in the patient, and one or more instruments are inserted through the cannula in order to reach the surgical site and to perform surgical operations.

Cannula seals are used to provide a seal between the cannula and the inserted instrument, for example against insufflation gas leakage. Therefore, there is a need to develop improved cannula seals for surgery.

SUMMARY

In accordance with aspects of the present invention, a cannula seal includes a cap portion, the cap portion fitting over a cannula; and a valve portion, the valve portion including an hourglass seal, and a cross slit seal. In some embodiments, the cap portion includes a tab. In some embodiments, the cap portion and the valve portion are integrally formed. In some embodiments, the cap portion and the valve portion are joined at a bonding region, which may include overflow traps. In some embodiments, ribs are included.

These and other embodiments are further discussed below with respect to the following figures.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the scope of the invention. For example, spatially relative terms—such as "beneath", "below", "lower", "above", "upper", "proximal", "distal", "horizontal", "vertical" and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Figure 1:
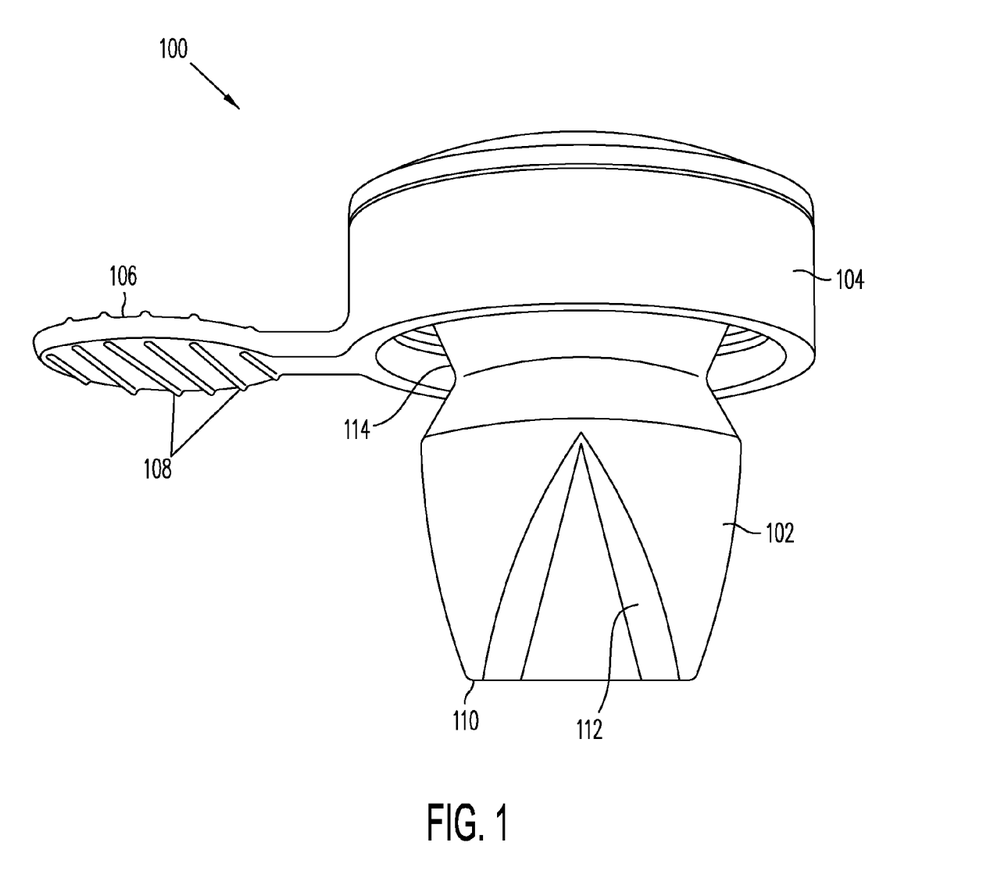
FIG. 1 illustrates a cannula seal according to some embodiments of the present invention.

FIG. 1 illustrates a cannula seal 100 according to some embodiments of the present invention. As illustrated in FIG. 1, cannula seal 100 includes a cap portion 104 and a valve portion 102, both of which may be formed, for example, of a polyisoprene rubber compound, silicone rubber, polyurethane elastomer, chlorobutyl rubber, ethylene propylene diene monomer ("EPDM") rubber, or other compound. As described in detail below, in some embodiments cap portion 104 and valve portion 102 are bonded together to form seal 100. Alternatively, seal 100 may be formed as a single continuous piece. Cap portion 104 allows seal 100 to mate with one end of a cannula (see e.g., FIG. 4). Valve portion 102 provides the seal function, both with and without an inserted instrument. As illustrated in FIG. 1, valve portion 102 includes a cross slit seal 110 and an hourglass seal 114.

Cross slit seal 110 is illustrative of various duckbill type valves that may be used. Such valves seal on themselves in the absence of an inserted instrument. Duckbill type valves are formed from an elastomeric tube formed with inward folded walls to hold an end of the tube together so as to form various numbers of slits, such as one (single duckbill), two (double duckbill; cross slit), three (trifold; joker-type). In the absence of an inserted object, the cross slit seal maintains its shape such that the two crossed slits are closed, thereby sealing against leakage across the seal. When an instrument is inserted through the seal, the seal resiliently deforms to allow the instrument to pass though. The resilient nature of the seal material keeps the slits close to the inserted instrument, and when the instrument is withdrawn, the seal returns to its closed position. As shown in FIG. 1, cross slit seal 110 is formed as two crossed slits 204 and 206 (shown in FIG. 2). In some embodiments, folded sidewalls 112 are concave. This concave shape helps to push the slits of seal 110 together in the presence of fluid pressure from outside the seal, such as from insufflation gas, because the force of the fluid near the slit is more directly across the slit.

Hourglass seal 114 is arranged to seal around an instrument when the instrument is inserted through seal 100. Although FIG. 1 illustrates an example with a single hourglass seal 114, multiple hourglass seals 114 can be included, stacked one atop another.

The interior diameter of hourglass seal 114 is sized to form a close fit with an instrument shaft when inserted through seal 100. This close fit may provide a slight clearance between hourglass seal 114 and the instrument shaft, or it may provide a slight friction fit. In some instances, hourglass seal 114 is sufficiently resilient that it will seal against instruments having different shaft diameters. For example, an hourglass seal 114 as depicted may provide sealing against both 12 mm and 13 mm instrument shaft diameters. Hourglass seal 114 provides an effective seal against an inserted instrument so that, for example, insufflation gas does not leak through seal 100 when an instrument is inserted. Cross slit seal 110 acts as a complement, providing an effective seal against, for example, insufflation gas leakage when the instrument is not inserted. Thus hourglass seal 114 and cross slit seal 110 work together to provide an effective seal against leakage through seal 100 whether or not an instrument is inserted.

As is further illustrated in FIG. 1, cap portion 104 includes a pull-off tab 106. Tab 106 assists the user in removing seal 100 from the top of a cannula. In some embodiments, tab 106 can include ridges 108 that enhance the user's grip on tab 106.

Figure 2:
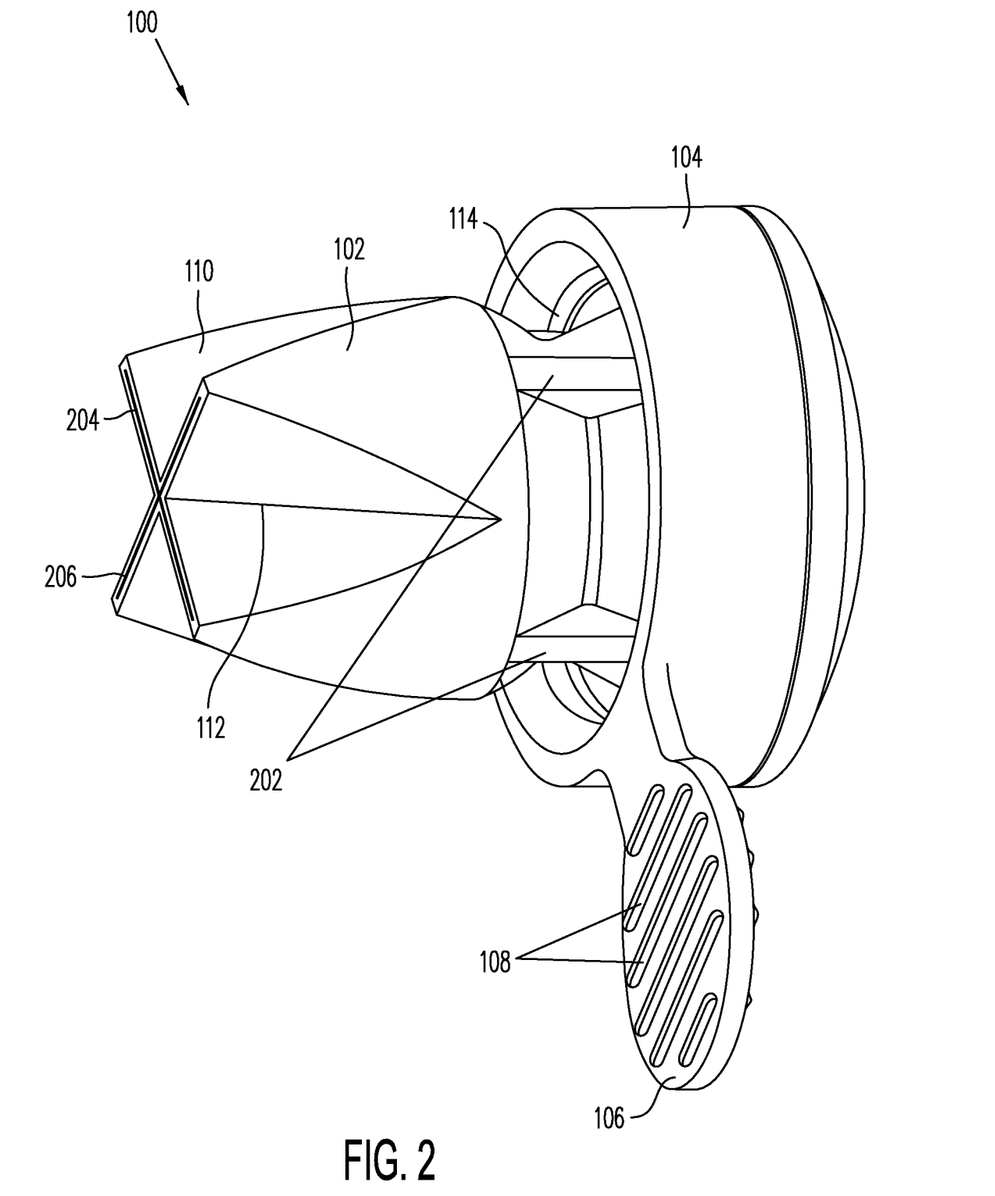
FIG. 2 further illustrates a cannula seal according to some embodiments of the present invention.

FIG. 2 illustrates some embodiments of seal 100. As shown in FIG. 2, slits 204 and 206 of cross slit seal 110 are clearly shown. Further, an example of folded sidewalls 112 is illustrated. As is also shown in FIG. 2, in some embodiments ribs 202 are formed around the outer perimeter of hourglass seal 114 in order to provide stiffening reinforcement for hourglass seal 114. Ribs 202 are formed integrally with hourglass seal 114, and hence with valve portion 102, so that the entire valve portion 102, including ribs 202, can be formed in, for example, a single injection molding process. In this way, the combined advantages of the hourglass and cross slit seals, plus the advantages offered by ribs 202, are formed as a single, inexpensively fabricated piece. The embodiment illustrated in FIG. 2 has four ribs 202 (two are hidden from view) spaced apart approximately 90 degrees around the outer perimeter of hourglass seal 114. In other embodiments, other numbers of ribs 202 may be formed, such as three or six. In some embodiments, ribs 202 may be positioned around hourglass seal 114 to be aligned with the one or more slits in the duckbill valve.

Ribs 202 provide several advantages for hourglass seal 114. First, ribs 202 add longitudinal (aligned from top to bottom) stiffness to hourglass seal 114 without substantially affecting the friction profile of hourglass seal 114. Thus, hourglass seal 114 is less likely to longitudinally deform as an instrument shaft moves through it—such longitudinal deformation causing a change in the friction profile between the instrument and seal. A relatively constant friction profile enhances smooth control, and may prevent or significantly reduce stick-slip, which is important during the constant insertion and withdrawal movements required in both manual and robotic surgery. Further, the enhanced longitudinal stiffness that ribs 202 provide for hourglass seal 114 can help to prevent cross slit seal 110 from being damaged or pulled through seal 100 by an instrument being removed from seal 100. Even if cross slit seal 110's sidewall starts to become inverted during instrument withdrawal, either from friction or from an instrument protrusion catching on an edge of a slit, the added longitudinal stability in hourglass seal 114 helps to prevent the cross slit seal from becoming fully inverted through the top of seal 100, which then must be corrected in order to insert another instrument, and to prevent resulting damage to the cross slit seal 110, which would then have to be replaced during surgery. Thus, stiffening ribs 202 enhance the advantages of using both hourglass seal 114 and cross slit seal 110 in a single seal 100, while improving the number of cycles of use (the number of times an instrument can be inserted and removed from seal 100) for seal 100.

Figure 3A:
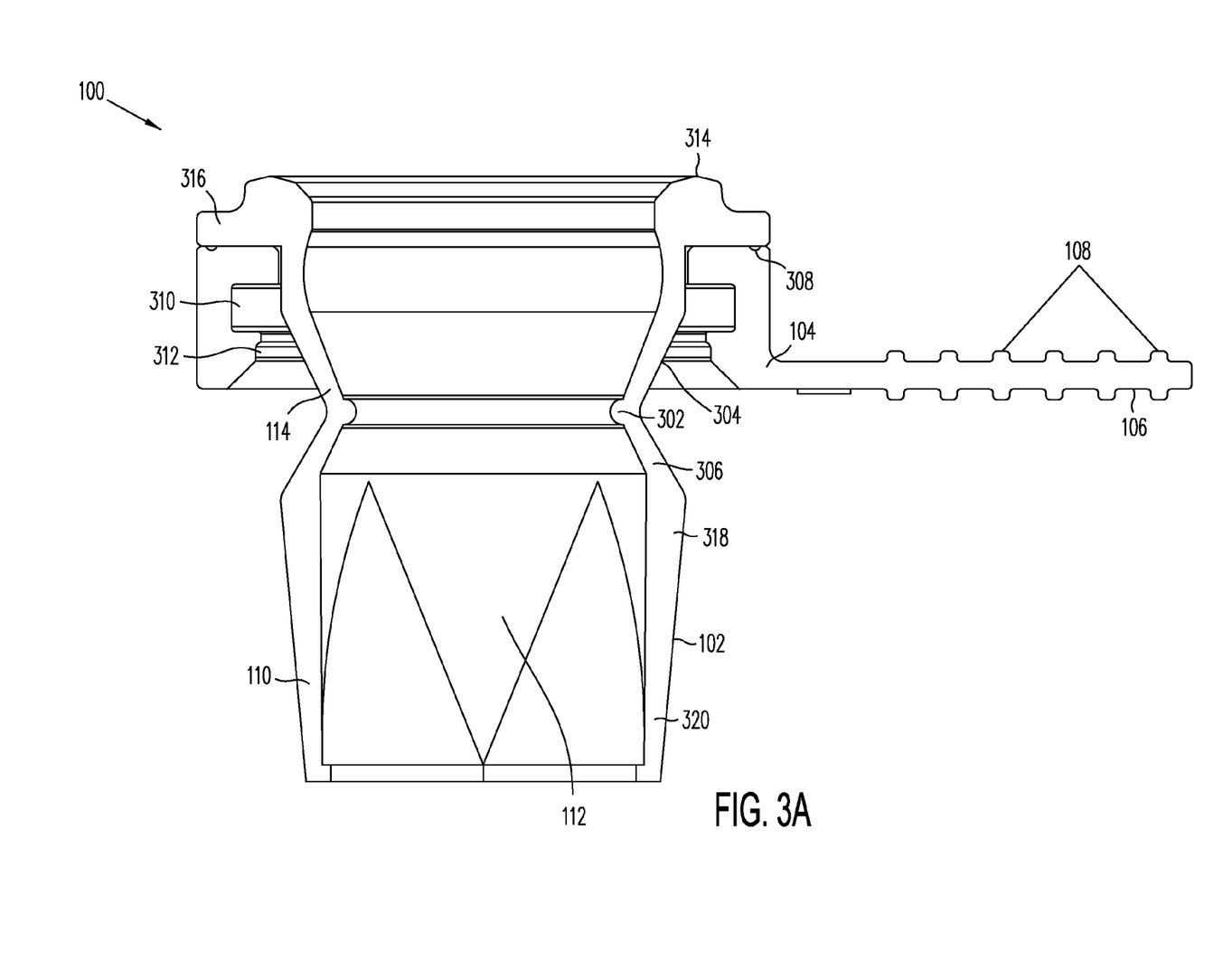
FIG. 3A illustrates a cross section of the cannula seal shown in FIG. 1.

FIG. 3A illustrates a cross section of an embodiment of seal 100. The cross section illustrated in FIG. 3A does not pass through ribs 202. As shown in FIG. 3A, cross slit seal 110 includes sidewalls with a relatively thick portion 318 at the top that taper to a relatively thin portion 320 towards the bottom, close to slits 206 and 204. Although the shape of the cross slit seal may be distorted by an inserted instrument, the relatively larger thickness (and consequent stiffness) of thick sidewall portion 318 helps to provide the ability of seal 110 to retain a round circumferential shape, and thus preserve cross slit seal 110's geometry for effective sealing. Further, the relatively smaller thickness (and consequent flexibility and tendency to seal) of sidewall portion 320 helps to provide an enhanced closure of slits 206 and 204 when an instrument is not present and may provide an enhanced seal between the folded sidewall 112 and the instrument when an instrument is inserted through the slits.

As shown in FIG. 3A, seal 114 is generally hourglass shaped (relatively larger diameter chambers joined by a relatively smaller diameter neck/waist region) and is formed from the sidewalls of two opposing generally cylindrical frustrums joined at their tops, shown as top sidewall 304 and bottom sidewall 306. Bottom sidewall 306 then joins with the thick top sidewall portion 318 of cross slit seal 110. Hourglass seal 114 is depicted as a lip seal that includes an 0-ring type protrusion 302 (the lip portion of the seal) that is integrally formed at the junction of the two sidewalls 304 and 306 in valve portion 102, at the "neck" of the structure, where the inner diameter is smallest. Protrusion 302 extends inward from the sidewall junction to further reduce the inner diameter of the hourglass seal. In some embodiments, more than one O-ring protrusion can be formed between sidewalls 304 and 306, the protrusions being positioned in a stacked series around the longitudinal axis.

In some embodiments, the O-ring type protrusion 302 may be omitted, so that either an annular flat or curved surface, or an annular vertex edge, is formed at the interior junction between sidewalls 304 and 306. Where applicable, features described in association with protrusion 302 are applicable in embodiments in which such a protrusion is not present.

In addition, although protrusion 302 is shown and described as an 0-ring type, it should be understood that other protrusion shapes may be used to provide, for example, an annular flat or curved surface, or an annular vertex edge.

Figure 3B:
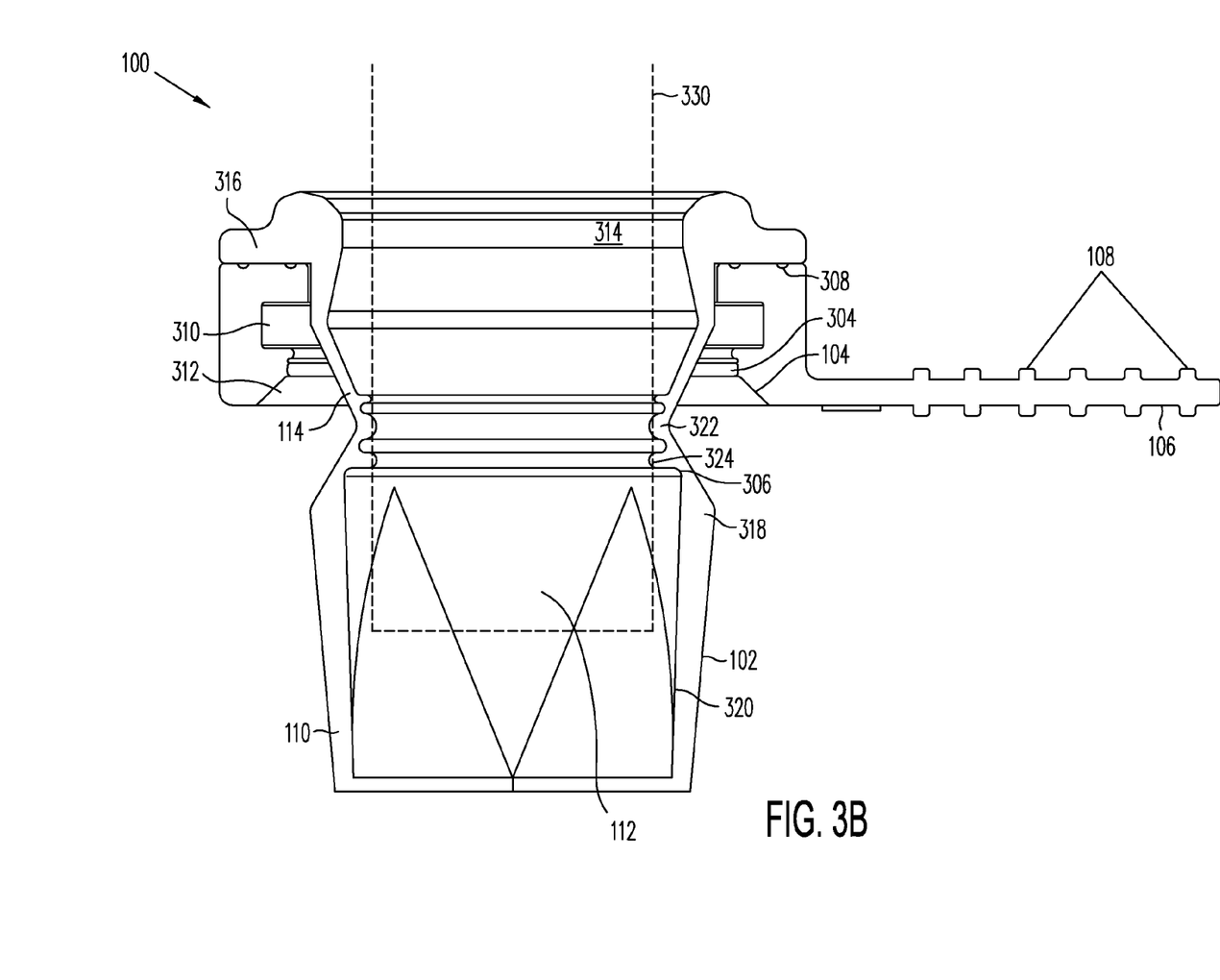
FIG. 3B illustrates a cross section of another embodiment of cannula seal as shown in FIG. 1.

In some embodiments, seal 114 can include more than one protrusion. For example, FIG. 3B illustrates an embodiment where, in place of protrusion 302, multiple protrusions, protrusions 322 and 324, are provided. As is shown in FIG. 3B, protrusions 322 and 324 may be formed with an inner diameter different from an inner diameter of one or more of the other protrusions, in order to accommodate a range of instrument shaft outer diameters. Further, in some embodiments lubricant can be provided between stacked O-ring protrusions 322 and 324 in order to provide and control lubricant applied to an instrument. In some embodiments, seal 114 can include any number of protrusions. FIG. 3B further illustrates an instrument 330 being inserted through seal 100.

Sidewalls 304 and 306 are shaped to support O-ring type protrusion 302 in such a way that some flexibility is allowed for lateral (aligned from side-to-side) motion of an instrument inserted into seal 100 and contacting O-ring protrusion 302. As shown in FIG. 3A, each or both of sidewalls 304 and 306 can be tapered to be thinner where they join one another. This tapering may allow O-ring protrusion 302 to be relatively more resilient from side to side during manipulation of an instrument than if the sidewalls had a constant thickness, thus maintaining a seal against an instrument even if the instrument is manipulated in a fashion that distorts O-ring protrusion 302 or moves O-ring protrusion 302 away from the seal's centerline longitudinal axis. In other words, the sidewall tapering towards the neck of the hourglass seal allows O-ring protrusion 302 to move with the inserted instrument while maintaining an effective seal against the instrument shaft. Further, in some embodiments sidewalls 304 and 306 can be longitudinally symmetrical in taper and extent. Such longitudinally symmetrical sidewalls 304 and 306 can provide a symmetrical friction profile for insertion and withdrawal of instruments inserted into seal 100, with resulting benefits as described above.

In some embodiments, O-ring protrusion 302's inner diameter is smaller than the outer diameter of the instrument that will be inserted into seal 100. A smaller diameter instrument can be accommodated by reducing the diameter of O-ring protrusion 302 accordingly. O-ring protrusion 302 themselves can be extended to reduce the diameter. In some embodiments, the dimensions of side walls 304 and 306 can be adjusted to accommodate a smaller diameter O-ring protrusion 302. The overlap diameter can be chosen to maintain a seal under various conditions and to provide low friction for insertion of the instrument. The overlap can be chosen as a compromise with the contrary considerations of low friction and high seal effectiveness.

Additionally, as shown in FIGS. 3A and 3B, cap portion 104 and valve portion 102 are joined at region 316 to form seal 100. One or more overflow traps 308 (one is shown in FIGS. 3A and 3B; two in FIG. 4) can be formed in either cap portion 104 or valve portion 102 as shown. Excess glue that is applied to the mating surfaces of cap portion 104 and valve portion 102 can be captured in overflow traps 308 before it overflows to an outside surface of valve portion 102 or cap portion 104. Any suitable glue, for example a medical grade cynoacrylate, can be used to bond cap portion 104 and valve portion 102 together. It should be understood that although the specific seal 100 embodiments are shown as being formed from separate cap 104 and valve 102 portions, for any design that can be accommodated by a relevant fabrication process, seal 100 may be formed as a single piece.

As shown in FIGS. 3A and 3B, an undercut region 310 is formed in cap portion 104 to receive a lip 404 of a cannula 402 (see FIG. 4) and to hold seal 100 on cannula 402. As an additional feature, top surface 314 of valve portion 102 can be rounded to help capture and guide an instrument into seal 100. Additionally, surface 312 of cap portion 104 can be shaped (e.g., chamfered as shown) to facilitate the insertion of cap portion 104 over lip 404 of cannula 402 so that lip 404 is seated within undercut region 310.

In some embodiments, cap portion 104 is formed of a material (e.g., one rubber compound) that is relatively stiffer than the material used to form valve portion 102 (e.g., another rubber compound) in order to more effectively hold seal 100 on cannula 402. Valve portion 102 can be formed of a relatively softer rubber in order that cross slit seal 110 and hourglass seal 114 are more compliant and seal more effectively. The use of one compound for cap portion 104 and another compound for valve portion 102 allows a material to be chosen that best suits the function of each portion. The stiffness and other desirable material features of each of valve portion 102 and cap portion 104 can be adjusted in various embodiments by adjusting the composition of the compound used in formation.

Figure 4:
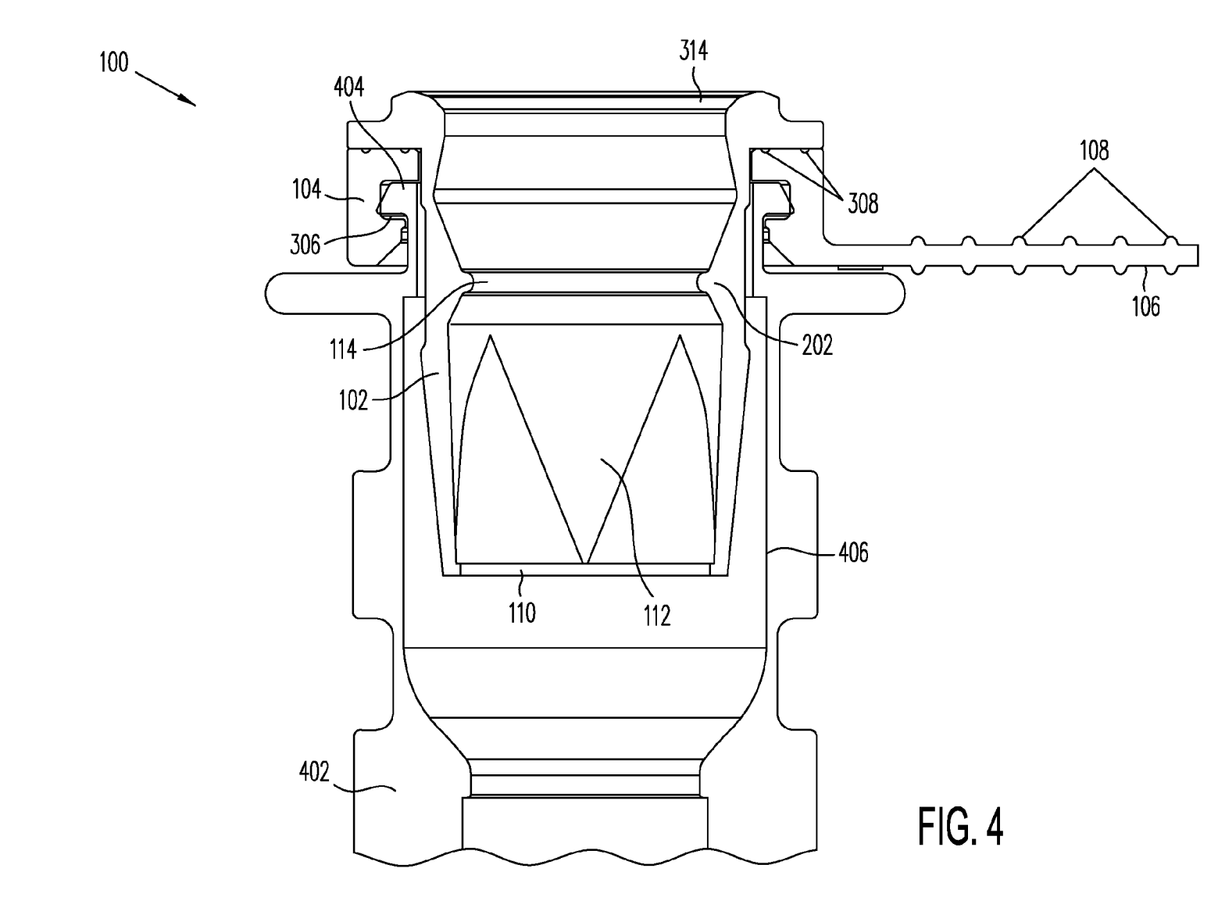
FIG. 4 illustrates an embodiment of a cannula seal according to the present invention inserted into a cannula.

Valve portion 102 and cap portion 104 can be formed, for example of isoprene rubber. In some embodiments, the isoprene rubber can be chlorinated, which reduces friction in cross slit seal 110 and in hourglass seal 114. In some embodiments, valve portion 102 and cap portion 104 can be formed of polyisoprene rubber, silicon, or urethane. In some embodiments, valve portion 102 and cap portion 104 can be made of a 30 A to 60 A durometer compound where valve portion 102 is a softer material than cap portion 104. FIG. 4 shows a cross section of a seal 100 embodiment attached to an illustrative cannula 402. Cannula 402 is shaped to receive seal 100, and seal 100 is shaped to be removably attached to cannula 402. As such, cannula 402 includes a lip 404 that is captured in undercut region 310. Further, cannula 402 includes a bowl at its proximal end (farther away from the surgical site and outside the patient) that receives seal portion 102. In the FIG. 4 illustration, the cross section of seal 100 is through ribs 202. As shown in FIG. 4, ribs 202 can contact an inner surface of cannula 402, and this contact reinforces hourglass seal 114. The resulting reinforcement helps to increase the longitudinal stiffness as described above, and also to provide lateral stiffness for the hourglass seal 114. The outer surface of ribs 202 can be shaped to provide either a small clearance with, or a slight friction fit against, the cannula's inner wall.

The above detailed description is provided to illustrate specific embodiments of the present invention and is not intended to be limiting. Numerous variations and modifications within the scope of the present invention are possible. The present invention is set forth in the following claims.

What is claimed is:

1. A cannula seal, comprising:
   a monolithic seal including a wipe seal portion and a cross-slit seal portion;
   the wipe seal portion including one or more sidewalls that form an hourglass having a neck portion and a plurality of ribs formed on the one or more sidewalks and extending across the neck portion, wherein the wipe seal portion is sized and shaped to seal against an instrument shaft when the instrument shaft is inserted through the wipe seal portion, wherein the plurality of ribs provides a consistent friction profile of the wipe seal portion during insertion and retraction of the instrument shaft by preventing longitudinal deformation of the hourglass as the instrument shaft moves through the wipe seal portion, and wherein the plurality of ribs provides structural support to prevent inversion of the cross-slit seal portion through the wipe seal portion when the instrument shaft is withdrawn through the cross-slit seal portion; and the cross-slit seal portion including a plurality of folded sidewalls that come together to define a plurality of slits sized and shaped to accommodate insertion of the instrument shaft through the cross-slit seal portion, wherein the cross-slit seal portion is sized and shaped to seal against insufflation gas flow through the cross-slit seal portion when the instrument shaft is not inserted through the cross-slit seal portion.

2. The cannula seal of claim 1, wherein the wipe seal portion includes an annular ring seal.

3. The cannula seal of claim 2, wherein the one or more sidewalls define an interior cavity, and the annular ring seal includes a first protrusion extending inward from the one or more sidewalls into the interior cavity, and a second protrusion proximate the first protrusion and extending inward from the one or more side walls into the interior cavity.

4. The cannula seal of claim 1, wherein the plurality of ribs includes a first rib that is aligned with a first pair of the folded sidewalls that come together to form a first slit and a second rib that is aligned with a second pair of the folded sidewalls that come together to form a second slit.

5. The cannula seal of claim 1,
wherein the wipe seal portion and cross-slit seal portion define a longitudinal instrument insertion axis along which the instrument shaft can be inserted;
wherein the one or more sidewalls are thinned proximate the neck portion to facilitate a side-to-side movement of the neck portion of the wipe seal portion; and
wherein when the instrument shaft is moved away from the longitudinal instrument insertion axis, the neck portion moves with the instrument shaft in a side-to-side movement and maintains an effective seal against the instrument shaft.

6. The cannula seal of claim 5, wherein the neck portion includes a first annular ring seal and a second annular ring seal proximate the first annular ring seal.

7. A monolithic cannula seal comprising:
means for sealing against an instrument shaft when an instrument shaft is inserted through the monolithic cannula seal, wherein the means for sealing against an instrument shaft includes an hourglass seal;
means for sealing against gas flow through the monolithic cannula seal when the instrument shaft is not inserted through the monolithic cannula seal, wherein the means for sealing against gas flow includes a cross-slit seal portion having a plurality of folded sidewalls that come together to define slits that allow the cross-slit seal portion to open to accommodate insertion of the instrument shaft past the cross-slit seal portion; and means for preventing longitudinal deformation of the monolithic cannula seal, providing a consistent friction profile during insertion and retraction of the instrument shaft, and preventing inversion of the means for sealing against gas flow as the instrument shaft moves through cannula seal, wherein the means for preventing longitudinal deformation includes a plurality of ribs formed around an outer perimeter of the hourglass seal, the plurality of ribs being aligned with the folded sidewalls to provide structural support to prevent the cross-slit seal portion from becoming fully inverted when the instrument shaft is withdrawn through the cross-slit seal portion.

8. A monolithic cannula seal comprising:
a proximal seal portion including a first side wall extending to define a proximal opening and an interior cavity, the proximal seal portion configured to seal against an instrument shaft that is inserted into the interior cavity;
a distal seal portion connected to and integrally formed with the proximal seal portion, the distal seal portion including first seal portions defining a first slit and second seal portions defining a second slit, the first slit and second slit forming a closable distal opening sized and shaped to allow the instrument shaft to pass through the closable distal opening, and the first seal portions and second seal portions configured to prevent insufflation gas from flowing proximally through into the interior cavity when the instrument shaft is not inserted through the distal seal portion;
a first rib on the proximal seal portion aligned with the first seal portions on the distal seal portion; and
a second rib on the proximal seal portion aligned with the second seal portions on the distal seal portion,
the first rib and second rib sized and shaped to prevent inversion of the distal seal portion when the instrument shaft is withdrawn through the distal seal portion and to support closure of the closable distal opening when the instrument shaft is not inserted through the distal seal portion.

9. The monolithic cannula seal of claim 8, wherein the proximal seal portion includes a second side wall, the second side wall meeting the first side wall at a neck, a cross-section of the interior cavity being smallest at the neck.

10. The monolithic cannula seal of claim 9, wherein the proximal seal portion includes first and second annular protrusions that extend inward at the neck, the first and second annular protrusions configured to seal against the instrument shaft that is inserted into the interior cavity of the proximal seal portion.

11. The monolithic cannula seal of claim 8, wherein the proximal seal portion includes a wipe seal, and the distal seal portion includes a cross-slit seal.

* * * * *